US012660994B2

(12) United States Patent
Buch et al.

(10) Patent No.: US 12,660,994 B2
(45) Date of Patent: Jun. 23, 2026

(54) ENDOSCOPE HAVING A DISTAL TIP UNIT WITH A BULGED PORTION

(71) Applicant: AMBU A/S, Ballerup (DK)

(72) Inventors: Ken Henrik Buch, Vordingborg (DK); Torben Svanberg Nielsen, Copenhagen (DK); Peter Bender Christoffersen, Kongens (DK)

(73) Assignee: AMBU A/S, Ballerup (DK)

( * ) Notice: Subject to any disclaimer, the term of this patent is extended or adjusted under 35 U.S.C. 154(b) by 333 days.

(21) Appl. No.: 18/217,884

(22) Filed: Jul. 3, 2023

(65) Prior Publication Data

US 2024/0008727 A1     Jan. 11, 2024

(30) Foreign Application Priority Data

Jul. 5, 2022     (EP) .................................... 22183110

(51) Int. Cl.
| | |
|---|---|
| *A61B 1/05* | (2006.01) |
| *A61B 1/00* | (2006.01) |
| *A61B 1/018* | (2006.01) |
| *A61B 1/06* | (2006.01) |

(52) U.S. Cl.
CPC ............ *A61B 1/05* (2013.01); *A61B 1/00045* (2013.01); *A61B 1/018* (2013.01); *A61B 1/0676* (2013.01)

(58) Field of Classification Search
CPC ....... A61B 1/05; A61B 1/00045; A61B 1/018; A61B 1/0676; A61B 1/00087; A61B 1/00096; A61B 1/0008; A61B 1/00101; A61B 1/0057; A61B 1/00137; A61B 1/00089

USPC ......................................... 600/127, 129, 175
See application file for complete search history.

(56) References Cited

U.S. PATENT DOCUMENTS

| | | | | |
|---|---|---|---|---|
| 5,235,965 | A | * | 8/1993 | Hiroya ............... A61B 1/00089 |
| | | | | 600/153 |
| 11,013,396 | B2 | | 5/2021 | Ouyang et al. |
| 11,229,454 | B2 | * | 1/2022 | Fonger ............ A61B 17/00234 |
| 11,291,352 | B2 | | 4/2022 | Vilhelmsen et al. |

(Continued)

FOREIGN PATENT DOCUMENTS

| | | |
|---|---|---|
| EP | 2797489 B1 | 2/2018 |
| EP | 3827731 A1 | 6/2021 |

(Continued)

OTHER PUBLICATIONS

Extended European Search Report for EP Patent Application No. 22183110.0, Issued on Dec. 16, 2022, 8 pages.

*Primary Examiner* — Anh Tuan T Nguyen
*Assistant Examiner* — Li-Ting Song
(74) *Attorney, Agent, or Firm* — Faegre Drinker Biddle & Reath LLP

(57) ABSTRACT

An endoscope including a handle or interface; and an insertion cord configured to be inserted into a patient's body cavity and including a distal tip; the distal tip including a distal tip housing and a camera module configured to be inserted into and accommodated in the distal tip housing; the distal tip housing including a tubular wall portion having an inner wall surface, an outer wall surface and a wall thickness, wherein the tubular wall portion comprises at least one bulged portion of increased wall thickness, the at least one bulged portion being formed on the outer wall surface in an area, where on the inner wall surface the camera module is arranged.

21 Claims, 4 Drawing Sheets

(56)  References Cited

U.S. PATENT DOCUMENTS

| | | | | |
|---|---|---|---|---|
| 11,730,344 B2 * | 8/2023 | Wales | | A61B 1/00101 |
| | | | | 600/127 |
| 2003/0088155 A1 | 5/2003 | Ishibiki | | |
| 2006/0173241 A1 * | 8/2006 | Ouchi | | A61B 1/31 |
| | | | | 600/128 |
| 2010/0240950 A1 * | 9/2010 | Heimberger | | A61B 1/307 |
| | | | | 600/104 |
| 2013/0172678 A1 * | 7/2013 | Kennedy, II | | A61B 1/2736 |
| | | | | 600/109 |
| 2018/0140177 A1 * | 5/2018 | Liu | | A61B 1/0052 |
| 2019/0191965 A1 * | 6/2019 | Ota | | A61B 1/0051 |
| 2019/0282070 A1 | 9/2019 | Vilhelmsen et al. | | |
| 2020/0237199 A1 * | 7/2020 | Levy | | A61B 1/00105 |
| 2021/0113056 A1 * | 4/2021 | Levy | | G02B 23/2423 |
| 2021/0153728 A1 | 5/2021 | Polluks et al. | | |
| 2021/0228064 A1 | 7/2021 | Sørensen et al. | | |
| 2021/0338057 A1 | 11/2021 | Satake | | |
| 2021/0386272 A1 | 12/2021 | Yamaya | | |
| 2022/0061645 A1 | 3/2022 | Jochumsen et al. | | |
| 2022/0095887 A1 | 3/2022 | Lent et al. | | |
| 2022/0313375 A1 * | 10/2022 | Zhang | | A61B 34/37 |
| 2023/0000325 A1 * | 1/2023 | Motohara | | A61B 1/0057 |
| 2023/0248434 A1 * | 8/2023 | Altshuler | | A61B 1/00091 |
| | | | | 600/108 |
| 2024/0023795 A1 * | 1/2024 | Gaworski | | A61B 1/0676 |
| 2024/0049952 A1 * | 2/2024 | Plott | | A61B 1/00006 |
| 2024/0172932 A1 * | 5/2024 | Mayer | | A61B 1/00137 |
| 2025/0213099 A1 * | 7/2025 | Keshtgar | | A61B 1/00149 |

FOREIGN PATENT DOCUMENTS

| | | |
|---|---|---|
| JP | 2008-036033 A | 2/2008 |
| WO | 2019/236415 A1 | 12/2019 |

* cited by examiner

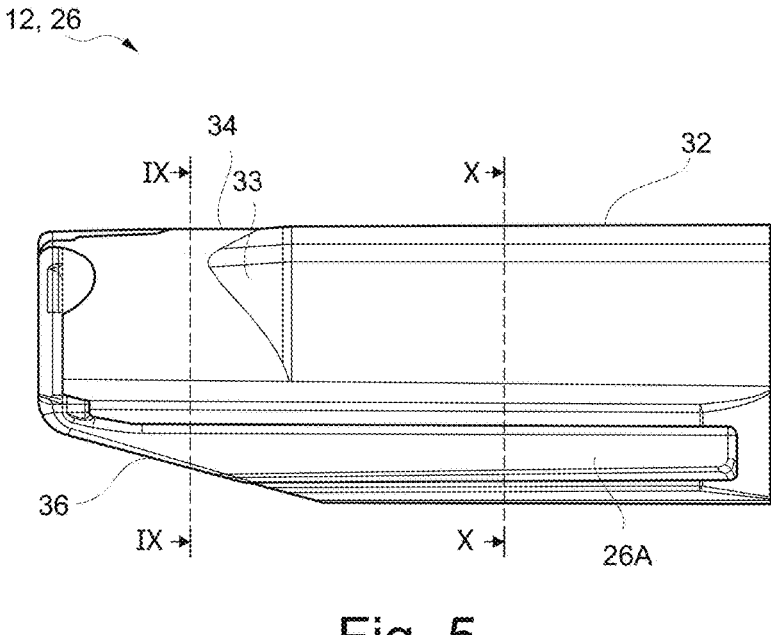
Fig. 5
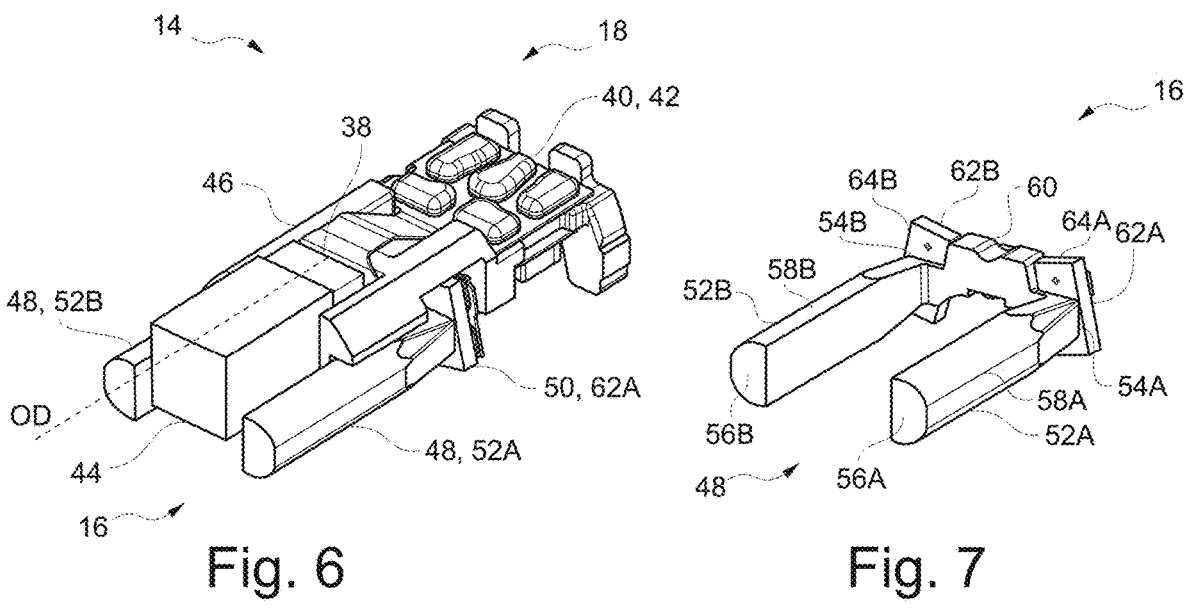
Fig. 6                    Fig. 7

ENDOSCOPE HAVING A DISTAL TIP UNIT WITH A BULGED PORTION

CROSS-REFERENCE TO RELATED APPLICATIONS

This application claims priority from and the benefit of European Patent Application No. EP 22 183 110.0, filed Jul. 5, 2022, which is incorporated by reference herein in its entirety.

TECHNICAL FIELD

The present disclosure relates to an endoscope comprising a distal tip. More specifically, the disclosure relates to an endoscope with a distal tip housing and a camera module accommodated in the distal tip housing.

BACKGROUND

Endoscopes are used for visual examination and diagnosis of hollow organs and body cavities, as well as to assist in surgery, e.g. for a targeted tissue sampling. Endoscopes can be reusable and disposable (i.e. single-use). Reusable endoscopes require cleaning and sterilization while single-use endoscopes are discarded rather than cleaned. Known endoscopes usually comprise an endoscope handle via which an operator/user can hold and control the endoscope, and an insertion cord comprising an insertion tube, an actively bendable bending section, and a distal tip that contains a light emitting device and an imaging device comprising e.g. an image sensor and a lens system so that the patient's body cavity can be illuminated and viewed by the operator/user, e.g. via a monitor connected to the endoscope.

Commonly owned U.S. Pat. No. 11,291,352, incorporated herein by reference in its entirety, discloses a single-use endoscope having an injection-moulded distal tip housing. Commonly owned U.S. Publication No. 2022/0061645 A1, incorporated herein by reference in its entirety, discloses a camera module adapted to be inserted into an open proximal end of the distal tip housing disclosed in U.S. Pat. No. 11,291,352. When using the distal tip housing disclosed in U.S. Pat. No. 11,291,352 and the camera module disclosed in U.S. Publication No. 2022/0061645 A1 in a small-diameter endoscope, such as a ureteroscope, a reduced outer wall thickness may be necessary to insert the camera module. The outer wall thickness maintains the structural integrity of the tip part during navigation of the endoscope in the patient and also the electrical integrity of the components inside the tip part. Reducing the outer wall thickness may introduce a risk of failure in the so-called high-potential (HIPOT) test, which is a high-voltage test to determine whether the electrical components can sustain voltages higher than peak operating voltages. If an electrical breakdown occurs through the distal tip housing, the tip housing has failed the test.

SUMMARY

The tasks and objectives of the present disclosure are to eliminate or at least reduce the disadvantages of the related art, especially the disadvantages of reducing the size of distal tip housing of the related art. More specifically, the problem addressed by the present disclosure is how to reduce the outer periphery of the tip part while maintaining as much internal space as possible, to allow insertion of a camera module, without increasing the risk of electrical failure. The risk of electrical failure may be higher where the wall thickness is too small or where the camera module has sharp edges or corners, since this may result in micro-scratches being created on the inner wall surface of the tubular wall portion of the distal tip housing when the camera module is inserted into the distal tip housing during manufacture or assembly.

Accordingly, an endoscope shall be provided which comprises a distal tip enabling safe operation of the electrical and optical components provided in the same even in case of a rather small outer outer diameter of the tip part.

In embodiments presented by the present disclosure, an endoscope comprises a distal tip comprising a distal tip housing and a camera module positioned inside the distal tip housing, the distal tip housing comprising a tubular wall portion having an inner wall surface, an outer wall surface, and a wall thickness that varies depending on the location of the camera module. In some variations, the tubular wall portion comprises at least one portion where the wall thickness is increased relative to other portions of the tubular wall. The thicker wall portion may be referred to as the "bulged" portion. The bulged portion may comprise material protruding/projecting radially outward from a cylindrical profile of a traditional tip housing. The bulged portions enabled successful HIPOT testing at 2.33 KV.

As mentioned, reducing the housing wall thickness may increase the risk of electrical breakdown. This risk is largest in areas where conductive parts of the camera module are closest to the housing wall. The risk may also be high in areas where the camera module has sharp edges or corners. Such micro scratches could be a reason for the distal tip unit to fail high-voltage testing. By providing or forming the at least one bulged portion, which may also be designated as shoulder or projecting/protruding portion, a small diameter distal tip may reliably pass the high-voltage testing, thus permitting safe operation of the electrical and optical components provided in the distal tip. Material is, preferably, only added locally in the area of the tip housing where a risk of electrical breakdown is estimated. The tubular wall portion of the distal tip housing is thus preferably not a (perfectly) cylindrical portion, i.e. is not (perfectly) circular seen in the cross section, due to the provision of the at least one bulged portion. The tubular wall portion may therefore be defined as having at least in portions a non-circular outer contour/circumference of the outer wall surface seen in the cross-section, wherein the non-circular outer contour/circumference is formed such that compared to a perfectly circular shape material is added in the form of the at least one bulged portion protruding radially further outward, wherein compared to a perfectly circular shape no material is removed, i.e. no recessed portion is provided in said portion of the tubular wall portion which comprises the at least one bulged portion.

The solution according to the present disclosure is advantageous compared to e.g. an embodiment according to which material is added around an entire circumference of the tubular wall portion, i.e. according to which the (outer) diameter of the outer wall surface is simply raised by providing the entire tubular wall portion with an increased wall thickness. In particular, the relevant outer dimension for endoscopic procedures is basically a length/external outline along an outer periphery around the distal tip unit in a cross sectional view, i.e. along an outer periphery in a plane extending perpendicular to a longitudinal axis of the distal tip housing. This length or external outline is recalculated to a corresponding circle diameter having a circumference corresponding to the mentioned length/external outline.

Therefore, the present disclosure provides an endoscope having a distal tip unit which suitably deals with the mentioned risk of electrical breakdown in the HIPOT test and at the same time has the mentioned circle diameter relevant for endoscopic procedures, which is only minimally increased due to the provision of the at least one bulged portion.

The endoscope according to the present disclosure is preferably a low-cost, lightweight, single-use endoscope, which is intended to be disposed after use in a single patient. This means that the endoscope is preferably optimized for one single use. The endoscope preferably has a limited number of elements, which are preferably manufactured with a low-cost material (polymer/plastic/resin) in preferably a low-cost manufacturing process (plastic/injection moulding) and which can be easily assembled.

The endoscope according to the present disclosure is, for example, a ureteroscope. However, the present disclosure is not limited to ureteroscopes. In particular, the endoscope according to the present disclosure may be another specialized endoscope, such as a bronchoscope, arthroscope, colonoscope, laparoscope, gastroscope, duodenoscope, cholangioscope, etc.

Preferably, the insertion cord of the endoscope is connected to the endoscope handle or interface and comprises an insertion tube, an actively bendable bending section and the distal tip unit extending in this order in the proximal-distal direction. Thereby, the bending section may comprise a plurality of bending segments being connected via hinges. Preferably, a proximal end segment of the bending section is the proximal-most bending segment of the plurality of bending segments and is preferably adapted to be connected to the insertion tube of the insertion cord. A distal end segment of the bending section is preferably the distal-most bending segment of the plurality of bending segments and is preferably adapted to be connected to the distal tip unit of the insertion cord. Said differently, the proximal end segment and the distal end segment are preferably designed/adapted such that they may be suitably connected to a remainder of the insertion cord and thus provide suitable interface parts fitting to the remainder of the insertion cord. The bending section may be injection molded as a one-piece part with hinges formed between adjacent segments.

The endoscope according to the present disclosure may be a one-plane bending endoscope configured to bend in two opposite directions (e.g. up-down). Alternatively, the endoscope may be a two-plane bending endoscope configured to bend in four directions (e.g. up-down and left-right). In order for the endoscope according to the present disclosure to be able to bend in two or four directions, steering wires may be provided, which run through the insertion cord, i.e. which in particular are lead from the endoscope handle or interface through the insertion tube to a distal end of the bending section. Thereby, for a one-plane bending endoscope, two steering wires may be provided, in particular on diametrically opposed portions of the insertion cord, whereas a two-plane bending endoscope may comprise four steering wires.

The endoscope according to the present disclosure is preferably a small-diameter endoscope, i.e. has rather small outer dimensions, in particular a rather small diameter of the insertion cord. The endoscope being a small-diameter endoscope preferably means that an outer diameter of the distal tip is less than 5 mm, preferably less than 4 mm, especially preferred less than 3 mm. The present disclosure thus preferably relates to a small and compact distal tip and therefore to a small and compact distal tip housing. As is well known, the diameter of a circle is the length of a line passing through the center of the circle. The area A of the circle is defined as $A=Pi*r^2$, where r is the radius of the circle. Thus, the diameter equals $2*sqrt(A/Pi)$, and because it is based on the area, the diameter can be calculated regardless whether the outer shape of the tip housing is cylindrical or bulged.

In case the endoscope is a small outer diameter one-plane bending endoscope, the outer diameter of the insertion cord is preferably less than 3.0 mm. In case the endoscope is a small outer diameter two-plane bending endoscope, the outer diameter of the insertion cord may preferably be less than 5.0 mm, e.g. between 4.0 mm to 4.5 mm. The present disclosure is not limited to the endoscope having an outer diameter in the mentioned ranges, the outer diameter may of course be larger than 5.0 mm.

Preferably, the distal tip housing comprises the tubular wall portion and a distal wall portion. The distal wall portion and the tubular wall portion are preferably integrally connected, i.e. monolithically formed. The distal wall portion is arranged distally with respect to the tubular wall portion. The tubular wall portion is preferably connected to a remainder of the insertion cord, i.e. in particular to the bending section.

The at least one bulged portion is preferably formed/provided at the tubular wall portion. Since the camera module is preferably inserted into the distal tip housing from a proximal end of the distal tip housing, the at least one bulged portion is thus advantageously provided right in the area/portion (seen in the longitudinal direction of the distal tip unit), where the camera module may be closest to the inner wall surface. The at least one bulged portion may or may not extend into the distal wall portion. Preferably, the at least one bulged portion does not extend along the entire axial length of the distal tip housing and does not extend into the distal wall portion of the tip housing. To be clear, the distal wall portion is at least in part tubular.

According to a preferred embodiment, the at least one bulged portion is formed as a projecting or protruding portion seen in a cross-section of the distal tip unit and has a specific axial length in the longitudinal direction of the distal tip unit. The specific axial length is preferably adapted to the camera module, such as to suitably deal with the problem of a component or portion of the camera module being close to and potentially scratching the inner wall surface of the distal tip housing when the camera module is inserted into the distal tip housing. For example, when the camera module is inserted/slid in the distal tip housing, there may be created a rather straight or linear scratch line on the inner wall surface of the distal tip housing, which is suitably dealt with by providing the at least one bulged portion having the specific axial length in the longitudinal direction of the distal tip unit and extending preferably straight/linearly. According to a preferred embodiment, the at least one bulged portion extends distally from a proximal end of the tubular wall portion, and thus from a proximal end of the distal tip housing, towards a distal end of the tubular wall portion.

When the distal tip comprises a working channel, the distal wall portion of the distal tip housing preferably comprises a slanted portion. In other words, the distal tip housing may be bullet-shaped. Preferably, a cross-sectional surface area of the distal tip housing reduces in the distal wall portion. Starting from the proximal end of the distal wall portion, the cross-sectional surface area of the distal tip housing may reduce, preferably continuously, towards the distal end of the distal portion.

According to a preferred embodiment, a main/majority portion of the tubular wall portion may have a first wall thickness and the at least one bulged portion of the tubular wall portion may have a second (maximum) wall thickness, wherein the second wall thickness preferably may be greater than the first wall thickness. E.g., the second wall thickness may be at least 25%, preferably at least 35%, greater than the first wall thickness. Said differently, the at least one bulged portion may be characterized by an increase in thickness of at least 25%, preferably at least 35% compared to an adjacent portion of the tubular wall portion of the distal tip housing in which the at least one bulged portion is not provided. According to a preferred embodiment, the first wall thickness may be between 0.10 mm and 0.20 mm, e.g. 0.18-0.20 mm, the second wall thickness may be between 0.20 mm and 0.30 mm, e.g. 0.25-0.27 mm. The increase in wall thickness, i.e. the difference between the second wall thickness and the first wall thickness may be between 0.05 mm and 0.10 mm, e.g. 0.07-0.08 mm. It has turned out that an overall tubular, i.e. cylindrical/circular appearance of the distal tip housing can be maintained when the wall thickness is only slightly increased in the at least one bulged portion, while at the same time occurrence of electrical breakdowns is prevented. When the distal tip comprises a working channel, the main portion surrounds the working channel and the bulged portion is opposite the working channel.

According to the present disclosure, a main portion of the tubular wall portion of the distal tip housing may be defined as a portion, the wall thickness of which is determined by structural integrity of the distal tip housing, i.e. the (first) wall thickness of the main portion is a minimal wall thickness, which is required in order for the distal tip housing to be suitably mouldable and to be able to accommodate the camera module. A user of the endoscope basically would like to have an endoscope having an insertion cord with an outer diameter which is as small as possible and would like to have a hollow space inside the insertion cord and thus also inside the distal tip unit which is as big as possible. Hence, the wall thickness of the main portion is a wall thickness, which is determined such that the hollow space inside the insertion cord can be made as large as possible, without endangering the structural integrity of the distal tip housing and without increasing the outer diameter of the distal tip unit.

Preferably, the tubular wall portion may comprise (at least) two bulged portions, the (at least) two bulged portion being both formed on the outer wall surface in an area/portion where on the inner wall surface the camera module is arranged. The provision of at least two bulged portions may be advantageous, in particular in case more than one component or portion of the camera module is close to, and in risk of scratching, on the inner wall surface of the tubular wall portion.

Further, according to a preferred embodiment, a distance between a point on the outer wall surface of the main portion (having the first wall thickness) may define a first radius of a first circle and a distance between a radially outermost point on the outer wall surface of the at least one bulged portion of increased wall thickness (second wall thickness) and a central axis of the tubular wall portion may define a second radius of a second circle, wherein the first radius is smaller than the second radius. Especially preferred, a first outer diameter corresponding to the first radius may be between 2.90 mm to 3.00 mm, e.g. 2.94 mm, and a second outer diameter corresponding to the second radius may be between 3.00 mm and 3.10 mm, e.g. 3.088 mm.

According to the preferred embodiment, in case two bulged portions are provided, the two bulged portions may be distanced by an angle of 45° to 135°, e.g. by 90°, in the circumferential direction. The angular distance between the two bulged portions may be measured by measuring the angle between the above-mentioned second radii of the two bulged portions. The angle may be measured where a point on the surface of the bulged portions is at a maximum distance away from the central, or longitudinal, axis of the tip housing.

Furthermore, according to a preferred embodiment, the distal tip housing may form a working channel, which may be provided or configured for insertion of a surgical tool or instrument into the patient's body cavity. Preferably, the working channel is provided mainly, i.e. for the most part, especially preferred entirely, on a first side with respect to a centre plane containing the central axis of the insertion cord, and the camera module is provided mainly, i.e. for the most part, on a second side with respect to said centre plane. The first side may be designated as working channel side and the second side may be designated as camera module side. The at least one bulged portion/the at least two bulged portions is/are preferably formed on the camera module side. Said differently, the at least one bulged portion may be formed in a first quadrant and/or a second quadrant of the cross-section and the working channel may be formed in a third quadrant and a fourth quadrant of the cross-section.

According to a preferred embodiment, the camera module may comprise a light emitting device and a light guide component (distally) connected to the light emitting device, wherein the light guide component may be configured to guide light out of the distal tip housing/the distal tip unit into the patient's body cavity. The light guide component may extend in an axial/longitudinal direction of the distal tip unit. Preferably, the at least one bulged portion may have the above mentioned specific axial length which is greater than or equal to the axial length of the light guide component.

In a preferred embodiment, the camera module may comprise at least one light emitting device, preferably two light emitting devices, and an imaging device. The imaging device may comprise an image sensor and a focusing system/lens system, such as a lens barrel.

Preferably, the distal tip housing is open at its proximal end, extends in a longitudinal/axial direction and forms a hollow (interior) space for accommodating the camera module.

The distal tip housing is preferably made from a polymer material, in particular a thermoplastic polymer material. The distal tip housing is preferably a monolithic part, and is especially preferred a moulded, such as injection-moulded part. E.g., the distal tip housing is manufactured/formed in a two-component injection moulding process.

Preferably, the distal tip housing comprises a first transparent part and a second opaque part. The first transparent part and the second opaque part may be described as fused or moulded together and form together the monolithic distal tip housing. The tubular wall portion may be essentially formed by the second, opaque, part. The first, transparent, part forms a distal end surface of the distal tip housing. However, it is to be understood that both the first transparent part and the second opaque part may be provided both in the tubular wall portion and the distal wall portion. It is to be understood that the terms "tubular wall portion" and "distal wall portion" serve to define two portions of the distal tip housing arranged next to each other in the longitudinal direction of the distal tip housing, and that the terms "first transparent part/portion" and "second opaque part/portion"

serve to define two portions of the distal tip housing being formed from different materials, namely from a transparent material and from an opaque material. A transition portion may be provided between the tubular wall portion and the distal wall portion to gradually reduce the cross-section of the tubular wall portion.

The camera module, in particular the imaging device, may include the image sensor viewing in an optical direction through the transparent portion of the distal tip housing.

The light-emitting device may comprise a light source preferably having a light-emitting surface and being configured to emit light, preferably from the light-emitting surface, in a central illumination direction, preferably the central illumination direction being at least partially oriented in the optical direction of the image sensor.

The imaging device may comprise the lens system including one or more lenses aligned with the optical direction and between the interior surface of the transparent portion and the image sensor so that the image sensor views through the lens arrangement and the transparent portion.

Preferably, the camera module may comprise, or be connected to, a printed circuit board, wherein the printed circuit board (PCB), in particular an electrical circuit provided on the printed circuit board, may be electrically connected with the imaging device and the light emitting device. The electrical circuit may comprise a first circuit portion in electrical communication with the image sensor and a second circuit portion in electrical communication with the light source. Thereby, the electrical circuit may be configured for transmitting an image signal generated by the image sensor indicative of the view in the optical direction, preferably to the endoscope handle. The light source may be an electrical component, such as one or more light-emitting diodes (LED), and the electrical circuit may comprise a second circuit portion in electrical communication with the light source. The electrical circuit provided on the printed circuit board may comprise a main circuit portion for interconnecting various electronic components, e.g. capacitors, transistors, and the like, of the printed circuit board. The first circuit portion of the electrical circuit may electrically connect the image sensor to the main circuit portion and the second circuit portion of the electrical circuit may electrically connect the light source with the main circuit portion. Thereby, the first circuit portion and/or the second circuit portion may be flexible so that, prior to assembly, the image sensor and light source(s) are movable relative to each other. In this case, the electrical circuit may be provided on a flexible (printed) circuit board (FPC). This may be an advantage in assembly, as the image sensor and light source (s) can be moved relatively to their desired position irrespective of production tolerances. The electrical circuit may be configured for transmitting the image signal to an electrical component, such as a circuit board, positioned in the endoscope handle. The image signal may be transmitted from the electrical circuit of the distal tip unit via a wired connection or a wireless connection. Thus, the electrical circuit does not necessarily comprise a cable extending between the distal tip unit and the endoscope handle for transmitting the image signal. The distal tip unit may comprise a frame part for supporting the electrical circuit. In particular, the electrical circuit may be provided on a folded FPC being folded around the frame part.

Further, the electrical circuit may also be arranged in the handle, and being connected separately to the first circuit portion (or the image sensor) and to the second circuit portion (or the LEDs).

According to a preferred embodiment, the at least one bulged portion may be formed in the area of the light source, in particular on an area of the outer wall surface on the inner wall surface side of which the light source is arranged. When inserting the camera module having the light source, in particular in the form of a LED, the LED, in particular an upper edge of the LED, may be placed close to the housing wall with risk of scratching on the inner wall surface of the distal tip housing. Hence, the flexible printed circuit board being arranged proximally of the LED and having the electrical circuit or electrical conductors would be placed very close to such a scratch, thereby increasing the risk of electrical breakdown.

Further, the camera module may comprise a light guide component connected to the light emitting device, the light guide component being configured to guide light out of the distal tip housing/the distal tip unit into the patient's body cavity. Preferably, the light guide component may comprise a first light guide having a light entry surface and a light exit surface, the first light guide being configured for propagating light received through the light entry surface out through the light exit surface and the transparent portion of the distal tip housing. Thereby, the first light source, the image sensor and the electrical circuit may be accommodated in the sealed hollow (interior) space of the distal tip housing, wherein the first light source may be attached, preferably directly attached, to the light guide component and preferably positioned proximally relative to the image sensor. By attaching the light source, preferably directly, to the light guide component, a loss of and variation in power of light due to varying offset position of the light source in relation to the light guide component can advantageously be prevented. Furthermore, the variance in a gap distance between the light source and the light guide component can be reduced or even avoided by directly attaching the light source to the light guide component. This has the advantage of reducing power losses and power variances. A further advantage is that such an arrangement is easier to assemble, especially when the distal tip unit is miniaturised as the light source and the light guide component may be an integrated assembly.

The light guide component may comprise a second light guide having a light entry surface and a light exit surface, the second light guide being configured for propagating light received through the light entry surface out through the light exit surface and the transparent portion of the tip housing. The distal tip unit may comprise a second light source having a light-emitting surface and being configured to emit light from the light-emitting surface in a central illumination direction to the light entry surface of the second light guide, preferably the central illumination direction of the second light source being at least partially oriented in the optical direction of the image sensor. A surface normal of the light-emitting surface of the second light source may be at least partially oriented in the optical direction of the image sensor.

The second light source may be attached, preferably directly attached, to the light guide component and preferably positioned proximally relative to the image sensor, such that the first and second light guides extend side-by-side or in parallel on opposite sides of the camera module, preferably the image sensor.

By having a light guide component with both a first and a second light guide, assembly of the distal tip unit is further improved as the light guides can be handled as a single component.

Additionally or alternatively, the distal tip housing may extend along a longitudinal axis and may comprise a wall extending circumferentially around the longitudinal axis. The wall may have a cylinder shell shape. The transparent portion may close off a distal end of the wall. Additionally or alternatively, the distal tip housing may be fanned as a monolithic piece. The transparent portion of the distal tip housing is preferably fanned of a transparent material. Additionally or alternatively, the distal tip housing may be manufactured by a single-shot injection moulding, preferably of a transparent material. This is a simple and cheap way of manufacturing the tip housing. Alternatively, the tip housing may be manufactured by a multi-shot injection moulding process comprising at least two shots. The wall may be formed by a shot, preferably of an opaque material, and the transparent portion may be formed by another shot, preferably of a transparent material. By forming part of the distal tip housing in a different material allows tailoring that part to have specific properties, for instance that part may be formed of an opaque material which may prevent stray light from entering the image sensor. Additionally or alternatively, the transparent portion may preferably be a window. The transparent portion may be formed in a distal end face of the distal tip housing.

Additionally or alternatively, the distal tip unit may comprise a plug sealing a proximal opening of the tubular wall portion, e.g. by an adhesive. The plug may be formed separately from the distal tip housing. In other words, the distal tip housing may comprise a distal end face and a proximal opening providing access to the hollow space, wherein the distal end face is preferably positioned opposite of the proximal opening, and wherein the distal end face comprises at least part of the exterior surface of the transparent portion, preferably the entirety of the exterior surface of the transparent portion.

Additionally or alternatively, the hollow space may be filled with air. In particular, the light guide(s) or the circumferential surface of the light guide(s) may be surrounded by air. The hollow space may be accessible by the proximal opening, and the distal tip housing may enclose the hollow space so that the proximal opening is the only access to the interior space. I.e. for assembling the distal tip unit, the camera module may be slid into the hollow space through the proximal opening.

Additionally or alternatively, the light source(s) may comprise a light-emitting diode configured for emitting substantially white light. The light-emitting diode may be a single light-emitting diode. Additionally, the light-emitting diode may be phosphor-based which is particularly suited, as it can emit white light and is compact. In any case, the light-emitting diode may comprise a semiconductor die surrounded by a cover which is typically epoxy-based. Alternatively, the light source(s) may comprise a plurality of light-emitting diodes, such as three, each configured for emitting a light of a different wavelength, such as red, green, and blue light. The plurality of light-emitting diodes may be covered by a cover and may be arranged so that the light emitted from the cover is substantially white. In both cases, an exterior surface of the cover may define the light-emitting surface of the light source(s). Alternatively, the light source(s) may comprise one or more optical fibres configured for transmitting light from an external light source, such as a light-emitting diode, positioned outside of the distal tip unit, such as positioned in the endoscope handle. The light-emitting surface(s) may thus form part of the one or more optical fibres.

Further, the endoscope according to the present disclosure may be a front-viewing endoscope. I.e. the optical direction of the image sensor may be parallel to the axial direction of the distal tip unit. However, the present disclosure is not restricted to front-viewing endoscopes, such that the optical direction of the image sensor may enclose an angle with the axial direction of the distal tip unit, in particular the optical direction of the image sensor and the axial direction of the distal tip unit may be perpendicular, thereby forming a side-viewing endoscope.

Preferably, a central illumination direction of the light source(s) may be at least partially oriented in, preferably parallel to, the optical direction of the image sensor. This may have the advantage of reducing light losses, as the redirection of the emitted light beam of the light source is reduced. The central illumination direction of the light source(s) may intersect the light entry surface of the corresponding light guide. Alternatively, the central illumination direction of the light source(s) may be substantially perpendicular to the optical direction of the image sensor. This has the advantage of allowing for a more compact arrangement of the light source(s).

Additionally or alternatively, the light guide exit(s) may comprise a collar at least partially surrounding the respective light guide, and the interior surface of the transparent portion may comprise a seat or seats for receiving the respective collar. Each seat may be formed as a rail or a depression for retaining the respective light guide. This may be advantageous for assembling the distal tip unit.

The second light guide may be identical or may be symmetric to the first light guide, and the second light source may be identical or may be symmetric to the first light source. This may improve the light distribution in the field of view of the image sensor.

Additionally or alternatively, the first and/or the second light source(s) may be at least partially overlapping the image sensor, when viewed in a cross-section perpendicular to the longitudinal axis. This has the advantage of allowing a more compact arrangement of the light source(s) and imaging device, as the light source(s) can be packed behind the image sensor and thus reduce(s) the combined diameter of the light source(s), and the imaging subassembly thereby allowing a smaller outer diameter of the distal tip housing.

Preferably, the first and/or the second circuit portion(s) may be flexible circuit structures, preferably so that, prior to assembly, the image sensor and light source(s) are movable relative to each other via flexing of first and/or second circuit portions. Since optimum optical performance is achieved by positioning the imaging device and light source(s) with a predetermined relative distance, the flexible circuit portion(s) has/have the advantage of allowing the assembler to move the parts relative to each other and thus absorb this variance.

Preferably, the light guide component may comprise the first and the second light guide being spaced apart by a gap and extending, preferably side-by-side or in parallel, along a respective longitudinal centre line, wherein each light guide has a proximal end, a distal end, a light entry surface at the proximal end, a light exit surface at the distal end, and a circumferential surface extending from the light entry surface to the light exit surface around the respective longitudinal centre line, and a cross-member extending transversely from the first light guide to the second light guide, preferably over the gap so as to form a unitary rigid light guide component, wherein the light guides are configured for propagating light received through the respective light entry surface out through the respective light exit surface, preferably while minimising light loss through the respective circumferential surface.

In the context of this disclosure, a light guide is not regarded as the same as an optical fibre. An optical fibre is typically long and thin, i.e. the length is several orders of magnitudes larger than the diameter and thus flexible providing the fibres with a high degree of flexibility to allow them to transmit luminous flux to a desired place without reshaping the light beam. Optical fibres are also typically arranged in a bundle. In contrast, a light guide is to be understood as much shorter, i.e. typically the length is within the same or one order of magnitude larger than the diameter, and preferably rigid, typically made in a single piece (e.g. monolithically formed) of a transparent material. A light guide also differs in function in that it is adapted to guide and reshape the incoming light beam in a desired manner. Further, an optical fibre typically comprises an opaque sheath while a light guide typically is monolithically formed without a sheath.

Additionally or alternatively, the light guide component is formed monolithically, and may preferably be manufactured by a moulding process, such as an injection moulding process. Preferably, the light guide component, i.e. the first light guide, second light guide, and the cross-member, is made of a single transparent polymer material. Thereby, it may be beneficial, when the light guide component may be manufactured by single-shot injection moulding, preferably of a transparent material. This is a simple way of manufacturing the light guide component. Alternatively, the light guide component may be manufactured by a multi-shot injection moulding process comprising at least two shots. The cross-member may be formed by a shot, preferably of an opaque material, and the first and second light guides may be formed by another shot, preferably of a transparent material. By forming part of the cross-member in an opaque material may prevent stray light from entering the image sensor.

Additionally or alternatively, the light entry surfaces of the first and second light guides may be planar and preferably parallel, and/or light exit surfaces of the first and second light guides may be planar and preferably parallel. In a preferably embodiment, all the light entry surfaces and the light exit surfaces are planar and parallel.

Additionally or alternatively, a gap may be located between the cross-member and the distal tip housing. The gap may be substantially uniform about the longitudinal axis. The gap may be sealed by an adhesive.

The distal tip housing may have a distal (front) end and a circumferential wall comprised of the tubular wall portion and the distal wall portion, and may comprise a first polymer material and a second polymer material, wherein the second polymer material is transparent. Thereby, the distal tip housing may be adapted to accommodate the camera module including the imaging device and the light-emitting device, i.e. the at least one light source. Further, the distal tip housing may comprise a first window part arranged in front of the imaging device in the field of view thereof, i.e. in the optical direction of the image sensor, and a second window part arranged in front of the at least one light source, wherein the first window part and the second window parts are formed as a single piece of said second polymer material. Furthermore, the distal tip housing may comprise an inwardly protruding part, wherein the inwardly protruding part may be formed integrally with the circumferential wall as a single piece of the first polymer material and/or integrally with said first and second window parts as a single piece of the second polymer material.

Preferably, the inwardly protruding part is adapted to guide and position the imaging device with respect to said first window part. This is an efficient way of assuring good positioning and alignment of the imaging device with respect to the first window part, so as to ensure low rejection rates in the manufacture of the disposable insertion endoscopes, in turn keeping costs down.

Alternatively, the at least one inwardly protruding part may be formed integrally with said first and second window parts as a single piece of the second polymer material comprises a light guide. By integration of the light guides in the single-piece item also comprising the first and second windows, the angular light distribution from LED light sources may readily be adapted to the field of view of the electronic vision device.

According to a preferred embodiment, the first housing material is opaque. This allows the introduction of shading parts inter alia reducing stray light and glare into the image sensor.

Further, the first housing material may have better adhesion properties to glue than the second material. This allows the circumferential wall of the distal tip housing to adhere efficiently to a sealing glue for sealing the hollow space (inner compartment), and for an outer sheath of the insertion tube of the endoscope to be securely adhered to the exterior or the interior of the circumferential wall of the pot-shaped housing.

Preferably, at the front end of the distal tip housing, said single piece of said first polymer material may partially cover said second polymer, so that the front window part and said light guide part may appear as separate areas isolated from each other by said first polymer, when viewed from the distal end. This has been found to highly reduce stray light and glare from the light source(s) into the image sensor.

Furthermore, the second housing material may be a thermoplastic material. This allows the tip housing to be produced in an efficient manner, such as by injection moulding.

The present disclosure further relates to a system comprising: an endoscope as described above; and a monitor connectable to the endoscope.

In other words and according to an aspect which may be independently claimed a distal tip housing of a distal tip unit of an insertion cord of an endoscope may be provided, the distal tip housing comprising a distal surface part and a tubular wall part extending from the distal surface part to a proximal end of the distal tip housing, the tubular wall part comprising a material having a first thickness over a majority of the tubular wall part, the tubular wall part having an outer cylindrically shaped surface with a circular cross-sectional shape, wherein the thickness has been increased to a second thickness in one or more selected areas by additional material placed exterior to the cylindrical shaped surface.

Thereby, an increase in thickness of the housing wall (tubular part) may be of at least 25%, preferably at least 35%. The increase in housing wall thickness may be added to limited parts of the exterior side of the outer surface of a cylindrical wall having a circular cross-sectional shape. Further, the tip housing may be made from a polymer material, and the housing may comprise transparent parts and opaque parts, wherein the transparent part and the opaque part may be fused together and may form the tip housing as a single piece of material. Therefore, the tip housing may be formed in a 2K moulding process. Furthermore, the distal tip may have a centre axis extending longitudinally from the distal surface to the proximal end. The tubular wall part may have a cross-sectional plane perpendicular to the centre axis wherein along the circumference there may be parts of the tubular wall with the first thickness and parts with the second thickness. Thereby, all such cross-sectional planes of the tubular wall part may have parts comprising at least the first thickness along the circumference.

In yet other words the present disclosure may relate to a distal tip housing comprising a distal wall part (distal wall portion) and a tubular wall part (tubular wall portion) extending from the distal wall part to a proximal end of the housing. The tubular wall part may comprise an outer surface and a cylindrical shaped plane with a centre axis and a radius R, i.e. the first radius r1. For a majority of the tubular wall part, i.e. the main portion, the cylindrical shaped plane may be coincident with the outer surface, and for an increased thickness part of the tubular wall part the outer surface may have a distance to the centre axis d, i.e. the second radius r2, which is larger than R. Hence, the tubular wall part may have a minimum thickness t and the thickness of the increased thickness part may be at least t+d−R. In other words, the main portion of the tubular wall portion may have the minimum thickness t, i.e. the first wall thickness, and the at least one bulged portion, the tubular wall portion may have the increased thickness, i.e. the second wall thickness, having the thickness $t2=t1+r2-r1$.

BRIEF DESCRIPTION OF THE DRAWINGS

The disclosure is explained in more detail below using preferred embodiments and referring to the accompanying figures.

FIG. 5 is a side view of the distal tip unit of the endoscope according to the preferred embodiment;

FIG. 6 is a perspective view of a camera module of the endoscope according to the preferred embodiment;

FIG. 7 is a perspective view of light emitting devices connected to light guide components of the endoscope according to the preferred embodiment;

The figures are schematic in nature and serve only to understand the disclosure. Identical elements are marked with the same reference signs. The features of the different embodiments can be exchanged among each other.

DETAILED DESCRIPTION

In the present disclosure "proximal" basically means "in a direction away from a patient towards a user" and "distal" basically means "in a direction towards the patient away from the user".

Figure 1:
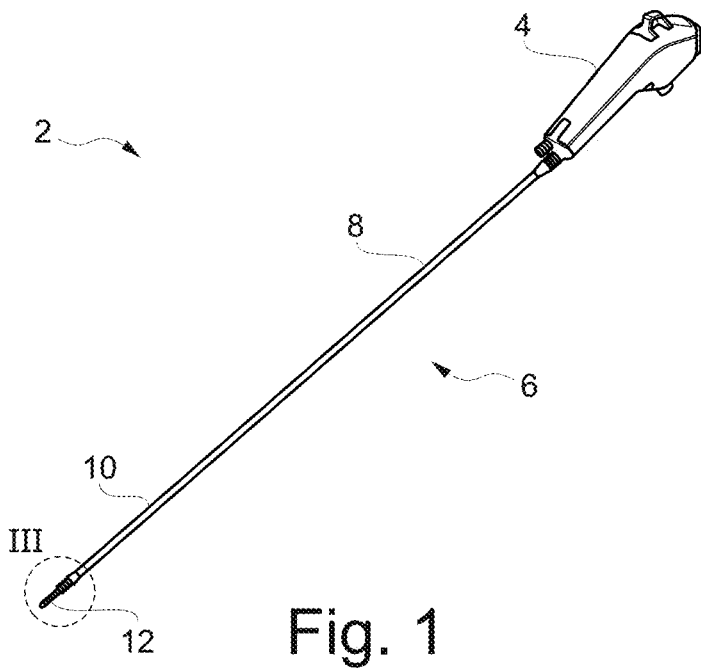
FIG. 1 is a perspective view of an endoscope according to a preferred embodiment.

An endoscope 2 according to a preferred embodiment of the present disclosure is shown in FIG. 1. The endoscope 2 is preferably a single-use or disposable endoscope, in particular a single-use ureteroscope for examination of the ureter of a patient. The endoscope 2 comprises a handle, or positioning interface, 4, and an insertion cord 6 extending distally from the handle and configured to be inserted into a patient's body cavity. The insertion cord 6 comprises an insertion tube 8, a bending section 10 and a distal tip, or tip unit, 12, which extend in this order from the handle 4. A camera module 14, comprising a light emitting device 16 and an imaging device 18, are positioned in a tip housing of the distal tip 12.

Figure 2:
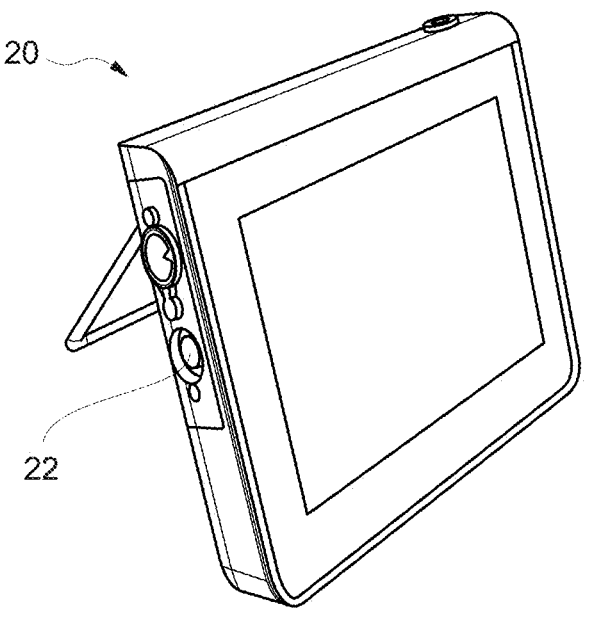
FIG. 2 is a perspective view of a monitor connectable to the endoscope according to the preferred embodiment.

FIG. 2 shows a monitor 20 of a visualization system 1 comprising the endoscope 2 and the monitor 20. Pictures/videos captured by the imaging device 18 of the endoscope 2 can be shown on the monitor 20, which is provided separately from, and connectable with, the endoscope 2. The monitor 20 comprises a cable socket 22 to which a monitor cable of the endoscope 2 (not shown) may be connected to establish signal communication between the endoscope 2 and the monitor 20. The monitor 20 displays images and/or videos captured by the imaging device 18 of the endoscope 2, thus allowing the user to see through the imaging device 18 of the endoscope 2.

Further, the endoscope 2 may have an internal working channel 24 accessible via an access port (not shown) provided at the endoscope handle 4 and via which a surgical tool or instrument can be guided into the patient's body cavity.

The endoscope handle 4 comprises a steering device (not shown), e.g. in the form of a handle wheel or a lever, which can be manipulated by the user in order to bend the bending section 10 for steering the distal tip 12. The steering device can be operated by the user to bend the bending section 10 in a bending plane, e.g. in an up-and-down direction. The endoscope 2 ma also be implemented as a two-plane bending endoscope having steering devices to steer the distal tip 12 up-and-down and right-and-left.

Figure 3:
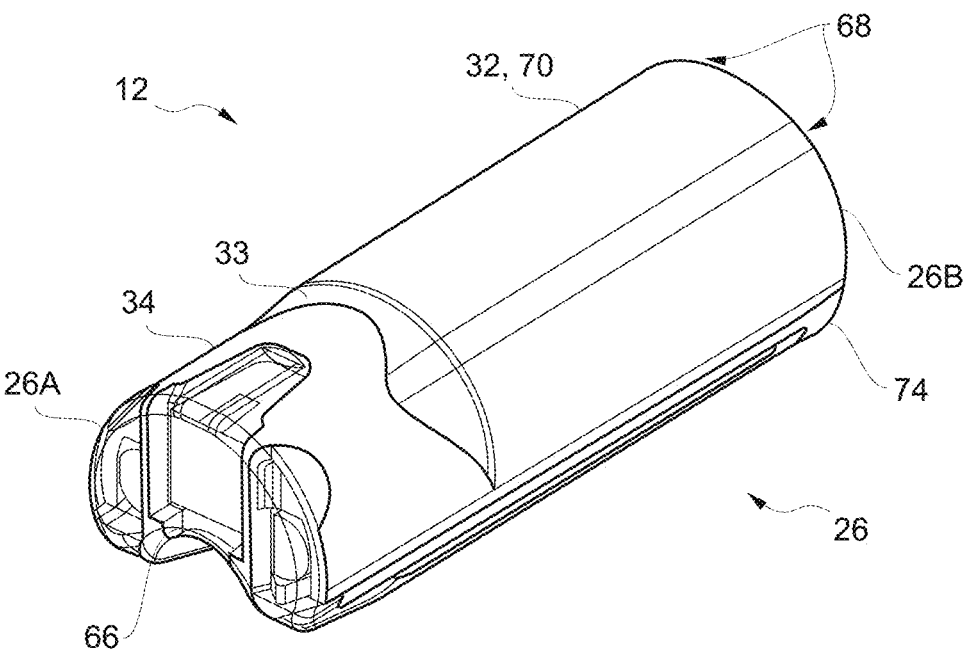
FIG. 3 is a perspective view of a distal tip unit of the endoscope according to the preferred embodiment.
Figure 4:
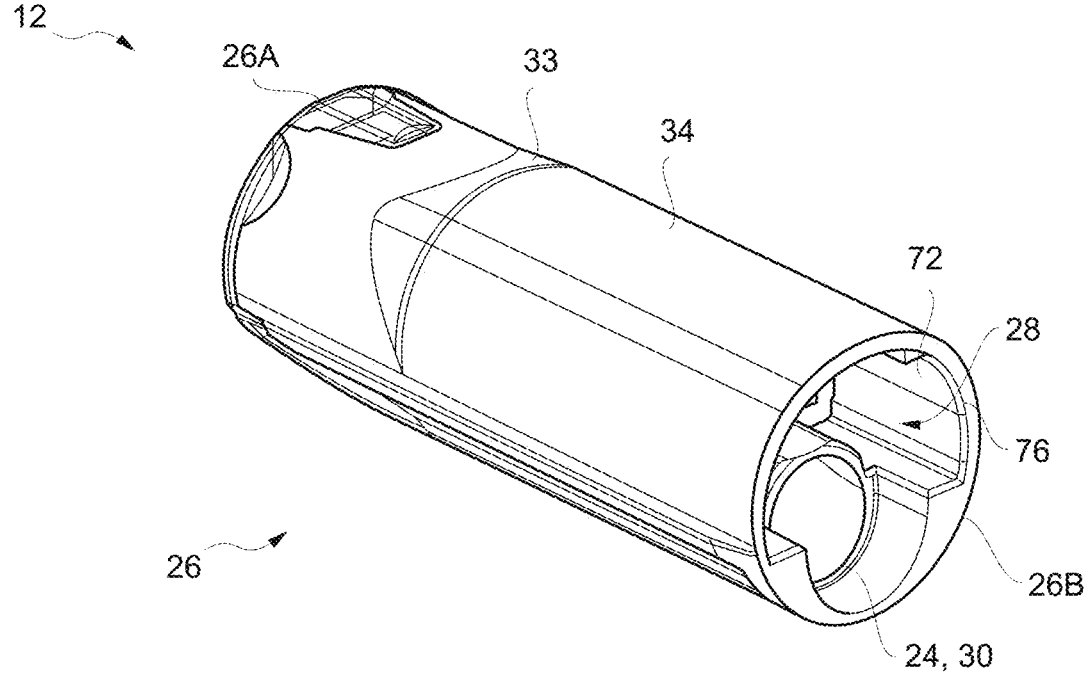
FIG. 4 is a perspective rear view of the distal tip unit of the endoscope according to the preferred embodiment.

An embodiment of the distal tip 12 is shown in FIGS. 3 and 4. The distal tip 12 comprises a distal tip housing 26 being formed as a sleeve, which is closed on its distal end and open at its proximal end. Hence, the distal tip housing 26 defines an interior, hollow space 28, which is accessible from a proximal end of the distal tip unit 12, as shown in FIG. 4. A passage is formed in the distal tip housing 26, which is provided to serve as a portion of the working channel 24 located in the distal tip unit 12. A working channel tube (not shown) extends from the handle 4 to the passage 30. The distal tip housing 26 comprises two housing components, namely a first housing component 26A and a second housing component 26B. The material compositions and optional manufacturing methods for forming the distal tip housing 26 are discussed further below.

The first housing component 26A comprises a window 66 which has a viewing section and light emitting sections. The second housing component 26B comprises a distal wall portion 34, a tubular wall portion 32, and a transition portion 33 therebetween, an outer wall surface 70, and an inner wall surface 72. The tubular wall portion 32 comprises a bulged portion 68, a main portion 74, and a proximal opening 76. The bulged portion 68 may be coextensive with the main portion 74 and diametrically opposite to it.

FIG. 5 shows a side view of the distal tip unit 12 illustrating the tubular wall portion 32 and the distal wall portion 34. The distal tip housing 26 has a slanted portion 36, such that a cross-section of the distal tip housing 26 reduces towards a distal end face of the distal tip housing 26. The slanted portion 36 enhances insertion of the distal tip unit 12 into the patient's body cavity. Provision of a working channel is optional. If the working channel is not provided, the slanted portion 36 can also be omitted. A cross-sectional view of the distal tip unit 12 shown as a plane X-X is discussed with reference to FIG. 9. This view includes the bulged portions 68. A cross-sectional view of the distal tip unit 12 shown as a plane IX-IX is discussed with reference to FIG. 10. This view is distal of the bulged portions 68. A transition section 33 of the tubular wall portion 32 is located between the bulged portions 68 and the distal portion 34 of the distal tip housing 26. The cross-section at the plane IX-IX is distal of the transition section 33. The side of the distal wall portion 34 opposite the slanted portion 36 may have a semi-cylindrical shape due to the absence of the bulged portions 68. The first housing component 26A comprises the window 66 and extending proximally from the window a pair of arms (one arm is visible in FIG. 5 extending to the proximal end of the distal tip housing) positioned in slots of the main portion of the tubular wall portion. The arms may facilitate molding and bonding of the first and the second housing components and may also provide structural support when molded from a more rigid material than the material of the second housing component.

FIG. 6 shows the camera module 14, including the light-emitting device 16, the imaging device 18 (also referred as a camera), and a camera module frame 46. The imaging device 18 is implemented with an image sensor 38 connected to an electrical circuit 40 provided on a flexible circuit board (FPC) or a printed circuit board 42, and a lens barrel 44 positioned distally of the image sensor 38. The lens barrel 44 encloses or supports lenses that optimise the view of the image sensor 38. The barrel forms an optical barrier preventing stray light from reaching the image sensor 38. The lens barrel 44 and the image sensor 38 view in an optical direction OD through the lens barrel 44. In the preferred embodiment, the optical direction OD is parallel to the axial direction of the distal tip unit 12, i.e. the endoscope 2 according to the preferred embodiment is a front-view endoscope. However, the optical direction OD and the axial direction might be oblique to each other, in particular perpendicular to each other thereby forming a side-view endoscope. The camera module frame 46 holds the light-emitting device 16. As shown, it comprises a proximal section supporting the printed circuit board 42 and two arms extending distally of the image sensor 38, each of the arms comprising a narrow wall positioned intermediate the lens barrel 44 and a light guide 52A, 52B.

The light-emitting device 16, as shown in FIG. 7, comprises a light guide component 48 and a light source 50. In the preferred embodiment, the light guide component 48 includes a first and a second light guide 52A, 52B spaced apart by a gap and extending in parallel along a respective straight longitudinal central centre line. Each light guide 52A, 52B has a proximal end, a distal end opposite of the proximal end, a light entry surface 54A, 54B at the proximal end, a light exit surface 56A, 56B at the distal end, and a circumferential surface 58A, 58B extending from the light entry surface 54A, 54B to the light exit surface 56A, 56B around the respective longitudinal central centre line. The light entry surfaces 54A, 54B of the first and second light guides 52A, 52B are planar and parallel, and the light exit surfaces 56A, 56B of the first and second light guides 52A, 52B are planar and parallel. Each of the circumferential surfaces 58A, 58B defines a polymer-air interface between the light guide component 48 and the hollow space 28. The light guide component 48 further includes a cross-member 60 extending transversely from the proximal end of the first light guide 52A to the proximal end of the second light guide 52B over the gap between the light guides 52A, 52B. The light guide component 48 is monolithically formed of a rigid and transparent polymer material with a refractive index that is higher than the refractive index of air. This ensures that the critical angle for total internal reflection of light incident on the circumferential surface 58A, 58B of each light guide 52A, 52B is also increased and thus increases the ability of the light guides 52A, 52B to propagate light from the respective light entry surface 54A, 54B to the respective light exit surface 56A, 56B and thereby minimising light loss through the circumferential surfaces 58A, 58B.

The light-emitting device 16 also comprises the light source 50. In the preferred embodiment, the light source 50 includes a first and a second light source 62A, 62B each formed of a light-emitting diode (LED), in particular a single phosphor-based light-emitting diode for emitting substantially white light. Each light source 62A, 62B comprises a single semiconductor die (not shown) for emitting light surrounded by an epoxy-based cover with an exterior surface forming a light-emitting surface 64A, 64B. The light-emitting surface 64A, 64B of each light source 62A, 62B is adhered to the light entry surface 54A, 54B of the respective light guide 52A, 52B by an adhesive so that light emitted by each light source 62A, 62B is propagated by the respective light guide 52A, 52B out through the window 66.

As described above, the image sensor 38 is connected to the electrical circuit 40 provided on the printed circuit board 42. Further, the printed circuit board 42 is in electrical communication with the light source 50, i.e. the first and second light sources 62A, 62B. The printed circuit board 42, in particular the electrical circuit 40, is configured for transmitting an image signal generated by the image sensor 38 indicative of the view in the optical direction OD to a circuit of the handle 4 of the endoscope 2 via several cables (not shown). It should be understood that as used herein the term "cable" denotes an insulated wire and the word "cables" denotes a plurality of insulated wires, which may or may not be enclosed in a sheath. Further, the printed circuit board 42, in particular the electrical circuit 40, is configured to receive commands from the circuit of the handle 4 in order to control the light source 50.

In the preferred embodiment, the endoscope 2 is implemented as the front-view endoscope. Hence, a surface normal of each light-emitting surface 64A, 64B is preferably oriented in parallel to the optical direction OD of the image sensor 38 so that light is emitted from the light sources 62A, 62B in the same direction as the view of the image sensor 38. The light guide component 48 is arranged so that the imaging device 18 occupies the gap between the light guides 52A, 52B and so that the light sources 62A, 62B are positioned proximally, i.e. behind, relative to the image sensor 38. This allows a more compact configuration of the camera module 14.

Figure 8:
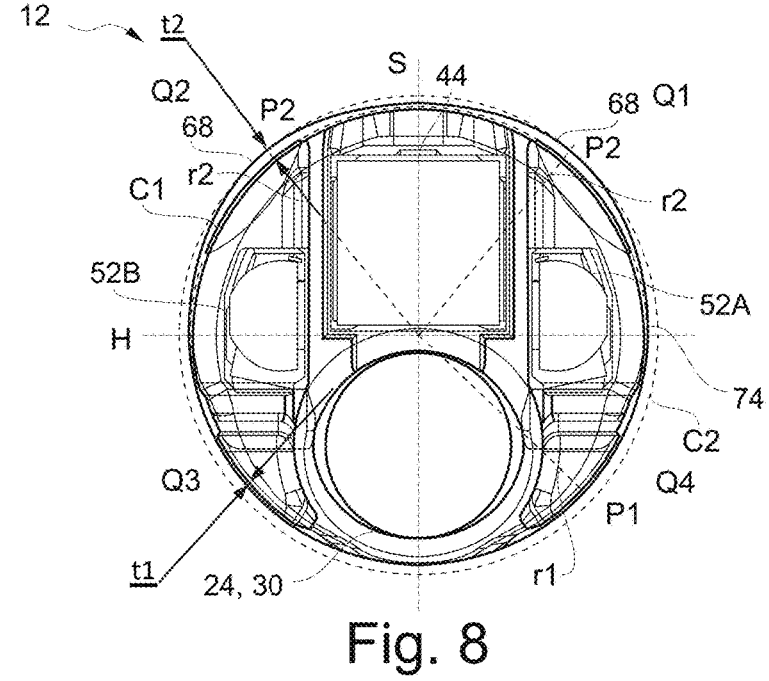
FIG. 8 is a front view of the distal tip unit of the endoscope according to the preferred embodiment.

FIG. 8 is a front view of a distal end face of the distal tip unit 12 according to the preferred embodiment. The light guides 52A, 52B and the lens barrel 44 are aligned with the first housing component 26A in the axial direction, such that light from the light sources 62A, 62B propagating through the light guides 52A, 52B can exit the distal tip unit 12 through the transparent, first housing component 26A. In addition, the lens barrel 44 in combination with the image sensor 38 can capture images through the first housing component 26A.

Figures 9, 10:
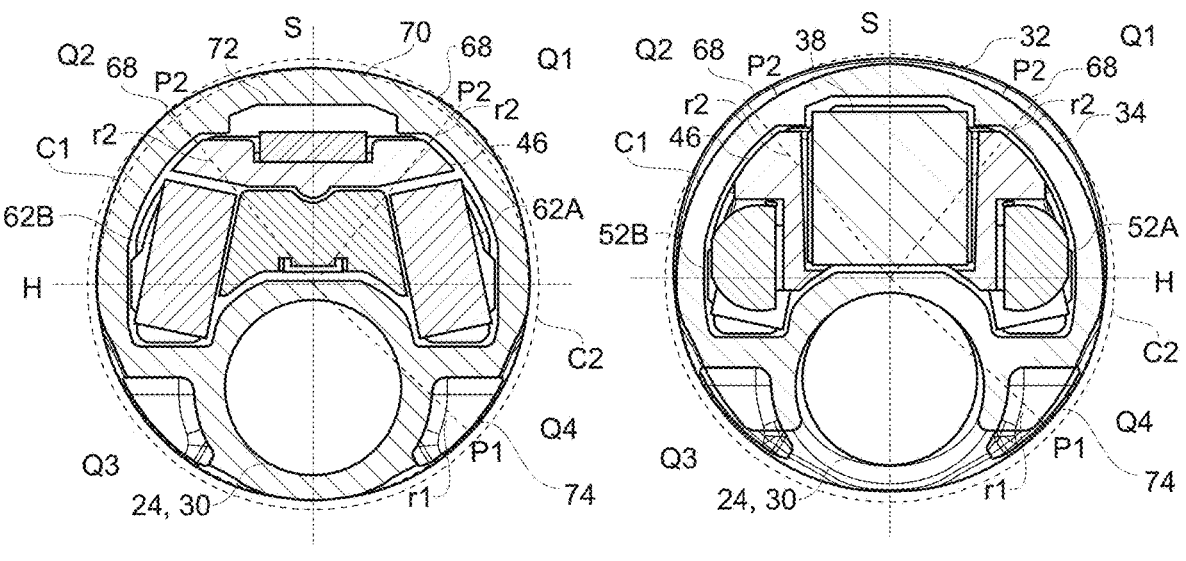
FIG. 9 is a cross-sectional view of the distal tip unit of the endoscope according to the preferred embodiment.
FIG. 10 is a further cross-sectional view of the distal tip unit of the endoscope according to the preferred embodiment.

As can be seen in FIGS. 8 and 9, the distal tip unit 12 has a substantially circular cross-section, which is symmetric relative to a symmetry plane S. The symmetry plane S is arranged between the first and second light guide 52A, 52B and extends through a centre point of the circular passage 30 or the working channel 24, respectively. In FIG. 9, a further horizontal plane H is shown, which is perpendicular to the symmetry plane S and extends through a centre axis of the distal tip unit 12, such that the distal tip unit 12 is divided into four quadrants Q1, Q2, Q3 and Q4.

FIG. 9 is a cross-sectional view of the distal tip unit 12 at an axial position, where the light source 50 is arranged, shown as a plane X-X in FIG. 5. As shown in FIGS. 8 and 9, according to the preferred embodiment, the distal tip housing 26, in particular the tubular wall portion 32, comprises two bulged portions 68 of increased wall thickness. The bulged portions 68 are formed on an outer wall surface 70 of the tubular wall portion 32 in areas/portions, where on an inner wall surface 72 of the tubular wall portion 32 the camera module 14, in particular the light source 50, is arranged. Further, as can be seen in FIGS. 8 and 9, the bulged portions 68 are formed on the outer wall surface 70 in areas corresponding to the first and second quadrant Q1 and Q2, whereas the passage 30 and the working channel 24 are formed and arranged in the third and fourth quadrant Q3, Q4. In other words, with respect to the distal tip unit 12 according to the preferred embodiment, the bulged portions 68 are formed on a camera module 14 side.

Accordingly, the tubular wall portion 32 comprises a main portion 74 having a first wall thickness t1 and the bulged portions 68 having a second wall thickness t2, wherein the second wall thickness t2 is greater than the first wall thickness t1. In the preferred embodiment, the second wall thickness t2 is about at least 25%, preferably at least 35%, greater than the first thickness t1. In other words, a circle C1, a radius r1 of which is defined by a line between a radial outermost point P1 of the main portion 74 and the centre point of the distal tip housing 26, is smaller than a circle C2, a radius r2 of which is defined by a line between a radial outermost point P2 of the bulged portion 68 and the centre point of the distal tip housing 26.

In the preferred embodiment, two bulged portions 68 are formed on the outer wall surface 70 of the tubular wall portion 32. Thereby, the radii r2 of the bulged portions 68, i.e. the lines connecting the centre point of the distal tip housing 26 to the radial outermost points P2 of each bulged portion 68, enclose an angle of approximately 90 degrees. In other words, the radii r2 of the bulged portions 68 are approximately perpendicular.

In other words, the distal tip housing 26 according to the preferred embodiment comprises two areas of the outer wall surface 70 of the tubular wall portion 32 with material added. A result of the added material is that an outer diameter of the tubular wall portion 32 is no longer constant but depends on an angle at which the outer diameter is measured. In the preferred embodiment, the outer diameter is measured to 2.94 mm in the horizontal plane H and in the approximately 20 degrees anticlockwise rotated outer diameter. However, measured in an approximately 45 degrees anticlockwise or clockwise rotation from the horizontal plane H, the distance from outer surface (radial outermost point P2) through the centre to the opposite outer surface is larger. Preferably, the wall thickness of the tubular wall portion 31 is increased from the first wall thickness t1 of about 0.187 mm to the second wall thickness of about 0.261 mm. I.e., the increase in material thickness is 0.074 mm.

FIG. 10 is a cross-sectional view of the distal tip unit 12 at a plane IX-IX shown in FIG. 5. As can be seen, the bulged portions 68 are not visible in the plane IX-IX because they terminate proximally of said plane. Hence, as shown in FIG. 5, in an axial direction of the distal tip housing 26, the bulged portions 68 extend from the proximal end of the distal tip housing 26 substantially to a portion of the distal tip housing 26 distal of the light sources 62A, 62B. The first and second light sources 62A, 62B, may be arranged across a light source plane traversing the bulged portions 68. The image sensor may be also be arranged across an image sensor plane traversing the bulged portions 68, which plane is distal of the light source plane traversing, both planes being orthogonal to the central axis of the distal tip housing.

Assembly of the distal tip unit 12 is performed as follows. The distal tip housing 26, a plug (not shown) being inserted into a proximal opening 76 of the distal tip housing 26 for closing the proximal opening 76, the light emitting device 16, the imaging device 18, and the printed circuit board 42 are provided as separately manufactured parts. The light emitting device 16, the imaging device 18 and the printed circuit board 42 are assembled on the camera module frame 46 in order to form the camera module 14. Thereby, the light-emitting surface 64A of the first light source 62A is adhered directly to the light entry surface 54A of the first light guide 52A and the light-emitting surface 64B of the second light source 62B is adhered directly to the light entry surface 54B of the second light guide 52B. This ensures that light emitted from the light sources 62A, 62B is received by the respective light guide 52A, 52B and transmitted out via the respective light exit surface 56A, 56B.

The assembled camera module 14 is then inserted through the proximal opening 76 into the hollow space 28 of the distal tip housing 26, by sliding the camera module 14 in the axial direction, so that the optical direction OD of the image sensor 38 extends through the window 66, and so that the light exit surface 56A, 56B of the first and second light guides 52A, 52B is oriented towards an interior surface of the window 66. The camera module 14 is pushed into the hollow space 28 until the light exit surfaces 56A, 56B and a distal end of the lens barrel 44 abut the interior surface of the window 66 simultaneously due to the prior relative adjustment. The camera module 14 is then adhered to the interior surface of the distal tip housing 26.

When the camera module 14 is pushed into the hollow space 28, there is a risk that conductive parts or sharp edges or corners of the camera module might come close to the inner housing wall. This may lead to a risk of electrical breakdown of the endoscope 2 during high potential testing. In order to prevent this risk, the bulged portions 68 are provided. Hence, by providing the bulged portions 68 having increased wall thickness only in areas, where scratches might occur, electrical breakdowns can be prohibited, without excessively increasing, i.e. with only minimally increasing an outer diameter of the distal tip unit 12.

After inserting the camera module 14, the plug (not shown) is inserted into and closes off the proximal opening 76 while allowing the above-mentioned cables to pass therethrough to the endoscope handle 4. An adhesive is applied between the plug and an interior housing surface to fluid and gas seal the hollow space 28. The distal tip unit 12 can then be assembled with the bending section 10, the insertion tube 8, and the endoscope handle 4, to form the endoscope 2 shown in FIG. 1.

The first housing component 26A and the second housing component 26B are manufactured from different materials or from different material compositions. For cost reduction, which is important for single-use endoscopes, materials used for the housing components 26A, 26B are preferably polymer materials, in particular thermoplastic materials suitable for injection moulding, but also thermoset materials and/or elastomers can be used. In particular, according to a preferred embodiment, the first housing component 26A and the second housing component 26B are manufactured from the same polymer material having different optical characteristics. I.e. the first housing component 26A and the second housing component 26B may basically be manufactured from a transparent polymer material, wherein a colour is mixed to said transparent material for the second housing component 26B, such that the material composition of the second housing component 26B is opaque and different from the first housing component 26A.

A material or material composition of the first housing component 26A, i.e. a first material composition, is preferably the transparent material without any colour added allowing light from the light emitting device 16 to pass and illuminate objects beyond the distal end of the distal tip unit 12. Accordingly, the first material composition should have good optical properties, e.g. in terms of transparency and high index of refraction. However, not all materials or material compositions render themselves for economically feasible manufacture and the use in environments for which the endoscope is intended. The first material composition is therefore preferably an injection mouldable polymer material such as polycarbonate, but other thermoplastic materials such as COP, COC and PMMA are also envisaged as are other polymer materials such as LSR (Liquid Silicone Rubber). One advantage of such softer and/or more elastic materials is their impact resistance.

A material or material composition of the second component 26B, i.e. a second material composition, on the other hand need not have good optical properties and may therefore be selected based on entirely different criteria. In particular, the second material or material composition may be an opaque material or, as stated above, the transparent material having added the colour to it. This will allow stray light from e.g. the light emitting device 16 to be absorbed and not disturb the images captured by the imaging device 18. In other words, if opacity is the only desire, the second material may consist substantially of the first material, i.e. the same polymeric material, with a filler or a dye (colour) added to make it opaque. This ensures that the first and second materials are very compatible, allowing them to bond well together and ensure a water and airtight distal tip housing 26. To achieve good tightness between the first material and the second material they are preferably moulded together to form one integrated unit in which the first material and the second material are fused during the molding process. A moulding process for forming the integrated unit is known from U.S. Pat. No. 11,291,352.

The following items are further variations and examples of the embodiments described with reference to the figures.

1. An endoscope (2) comprising a proximal endoscope handle (4) or interface; and an insertion cord (6) configured to be inserted into a patient's body cavity and comprising a distal tip unit (12); the distal tip unit (12) comprising a distal tip housing (26) and a camera module (14) configured to be inserted into and accommodated in the distal tip housing (26); the distal tip housing (26) comprising a tubular wall portion (32) having an inner wall surface (72), an outer wall surface (70) and a wall thickness, wherein the tubular wall portion (32) comprises at least one bulged portion (68) of increased wall thickness, the at least one bulged portion (68) being formed on the outer wall surface (70) in an area, where on the inner wall surface (72) the camera module (14) is arranged.

2. The endoscope (2) according to item 1, wherein a main portion (74) of the tubular wall portion (32) has a first wall thickness and the bulged portion (68) of the tubular wall portion has a second wall thickness, and the second wall thickness is greater than the first wall thickness.

3. The endoscope (2) according to item 2, wherein the second wall thickness is at least 25%, preferably at least 35%, greater than the first thickness.

4. The endoscope (2) according to any one of the preceding items 1 to 3, wherein the tubular wall portion (32) comprises two bulged portions (68) of increased wall thickness, the two bulged portion (28) being both formed on the outer wall surface (70) in the area, wherein on the inner wall surface (72) the camera module (14) is arranged.

5. The endoscope (2) according to item 4, wherein the two bulged portions (68) are distanced by an angle of 45° to 135° in the circumferential direction of the distal tip unit (12).

6. The endoscope (2) according to any one of the preceding items 1 to 5, wherein a distance between a point on the outer wall surface (70) of the main portion (74) and a central axis of the tubular wall portion (32) defines a first radius of a first circle and a distance between a radially outermost point on the outer wall surface (70) of the at least one bulged portion (68) of increased wall thickness and the central axis of the tubular wall portion (32) defines a second radius of a second circle, wherein the second radius is greater than the first radius.

7. The endoscope (2) according to any one of the preceding items 1 to 6, wherein the distal tip housing (26) forms or comprises a working channel (24) being provided for insertion of a surgical tool or instrument into the patient's body cavity.

8. The endoscope (2) according to item 7, wherein the at least one bulged portion (68) is formed on a camera module (14) side being diametrically opposed to a working channel (24) side of the distal tip housing (26).

9. The endoscope (2) according to any one of the preceding items 1 to 8, wherein the tubular wall portion (32) has a non-circular cross-section and the at least one bulged portion (68) is formed in a first quadrant and/or a second quadrant of the cross-section when viewed from a distal end of the distal tip unit (26).

10. The endoscope (2) according to item 9, wherein the working channel (24) is formed in a third quadrant and a fourth quadrant of the cross-section.

11. The endoscope (2) according to any one of the preceding items 1 to 10, wherein the camera module (14) comprises a light guide component (48) connected to the light emitting device (16), the light guide component (48) being configured to guide light out of the distal tip housing (26) into the patient's body cavity and extending in an axial direction of the distal tip unit (12), wherein the at least one bulged portion (68) extends for at least an axial length of the light guide component (48) in the axial direction of the distal tip unit (12).

12. The endoscope (2) according to any one of the preceding items 1 to 11, wherein the distal tip unit (12) comprises the tubular wall portion (32) and a distal portion (34) comprising a slanted portion (36).

13. The endoscope (2) according to any one of the preceding items 1 to 12, wherein the distal tip housing (26) comprises a first transparent portion and a second opaque portion.

14. System comprising: an endoscope (2) according to any one of the preceding items 1 to 13; and a monitor (20) connectable to the endoscope (2).

The term "comprising," "including," and "having," and variations thereof, are open transition terms that specify the presence of stated features, integers, steps or components but do not preclude the presence or addition of one or more other features, integers, steps, components or groups thereof. By contrast, the term "consisting" is a closed transition term that precludes the presence or addition of one or more other features, integers, steps, components or groups thereof.

LIST OF REFERENCE SIGNS 2 endoscope
4 endoscope handle
6 insertion cord
8 insertion tube
10 bending section
12 distal tip unit
14 camera module
16 light emitting device
18 imaging device
20 monitor
22 cable socket
24 working channel
26 distal tip housing
26A, 26B housing components
28 hollow space
30 passage
32 tubular wall portion
34 distal portion
36 slanted portion
38 image sensor
40 electrical circuit
42 printed circuit board
44 lens barrel
46 camera module frame
48 light guide component
50 light source
52A, 52B light guide
54A, 54B light entry surface
56A, 56B light exit surface
58A, 58B circumferential surface
60 cross-member
62A, 62B light source
64A, 64B light-emitting surface
66 window
68 bulged portion
70 outer wall surface
72 inner wall surface
74 main portion
76 proximal opening

We claim:

1. An endoscope comprising:
a handle; and
an insertion cord comprising a distal tip;
the distal tip comprising a distal tip housing and a camera module positioned inside the distal tip housing, the camera module comprising an image sensor, a first light emitting diode and a second light emitting diode, a symmetry plane of the distal tip housing traversing the camera module, the first light emitting diode being located on one side of the symmetry plane and the second light emitting diode being located on an opposite side of the symmetry plane, a horizontal plane being orthogonal to the symmetry plane and encompassing a center axis of the distal tip housing, the distal tip housing including a tubular wall portion and a distal wall portion distal of the tubular wall portion, the tubular wall portion having an inner wall surface, an outer wall surface, and a wall thickness, and the distal wall portion comprising a window longitudinally aligned with the camera module,
wherein the tubular wall portion comprises a first bulged portion, a second bulged portion, and a main portion coextensive at least in part with the first bulged portion and the second bulged portion, the wall thickness at the first bulged portion and the second bulged portion being greater than the wall thickness at the main portion, the first bulged portion and the second bulged portion extending distally from a proximal end of the distal tip housing toward but no further than the window,
wherein the first bulged portion and the second bulged portion are located on opposite sides of the symmetry plane and on a side of the horizontal plane, the main portion extending from the first bulged portion to the second bulged portion on an opposite side of the horizontal plane,
wherein the tubular wall portion is not circular, as seen in a cross section, at least due to the presence of the first bulged portion and the second bulged portion, and
wherein the first bulged portion extends distally at least as far as the image sensor.

2. The endoscope of claim 1, wherein the distal tip housing comprises a transition portion between the tubular wall portion and the distal wall portion, and wherein the first bulged portion and the second bulged portion end in the transition portion.

3. The endoscope of claim 1, wherein the wall thickness at the first bulged portion of the tubular wall portion is at least 25% greater than the wall thickness at the main portion.

4. The endoscope of claim 3, wherein the wall thickness at the first bulged portion is at least 35% greater than the wall thickness at the main portion.

5. The endoscope of claim 1, wherein the first bulged portion and the second bulged portion are distanced by an angle of 45° to 135° in the circumferential direction of the distal tip.

6. The endoscope of claim 1, wherein a distance between a point on the outer wall surface of the main portion and a central axis of the tubular wall portion defines a first radius of a first circle and a distance between a radially outermost point on the outer wall surface of the first bulged portion and the central axis defines a second radius of a second circle, wherein the second radius is greater than the first radius.

7. The endoscope of claim 6, wherein the first radius is between 2.0 and 3.0 mm and the second radius is between 3.0 and 3.1 mm.

8. The endoscope of claim 1, wherein the distal tip housing forms or comprises a portion of a working channel being provided for insertion of a surgical tool or instrument into a patient's body cavity.

9. The endoscope of claim 8, wherein distal tip housing comprises a camera module side and a working channel side diametrically opposite the camera module side, the first bulged portion being formed on the camera module side.

10. The endoscope of claim 1, wherein the tubular wall portion has a non-circular cross-section, the first bulged portion is formed in a first quadrant, the second bulged portion is formed in a second quadrant, and a working channel is formed in a third quadrant and a fourth quadrant, of the cross-section when viewed from a distal end of the distal tip.

11. The endoscope of claim 1, wherein the image sensor is arranged across an image sensor plane traversing the first bulged portion, the image sensor plane being orthogonal to the center axis of the distal tip housing.

12. The endoscope of claim 1, wherein the distal wall portion comprises a slanted portion.

13. The endoscope of claim 1, wherein the distal tip housing comprises a first, transparent, portion and a second, opaque, portion, the second portion comprising the tubular wall portion.

14. A visualization system comprising:

the endoscope of claim 1; and a monitor connectable to the endoscope.

15. The endoscope of claim 1, wherein the wall thickness at the main portion is between 0.10 mm and 0.20 mm, and wherein a maximum wall thickness at the first bulged portion is between 0.20 mm and 0.30 mm.

16. The endoscope of claim 1, wherein a difference between the wall thickness at the main portion and a maximum wall thickness at the first bulged portion is between 0.05 mm and 0.10 mm.

17. The endoscope of claim 1, wherein a distance between a point on the outer wall surface of the main portion and the center axis defines a first radius of a first circle, and wherein the first radius is constant along the main portion.

18. An endoscope comprising:

a handle; and an insertion cord comprising a distal tip;

the distal tip comprising a distal tip housing and a camera module positioned inside the distal tip housing, the camera module comprising an image sensor, a first light emitting diode and a second light emitting diode, a symmetry plane of the distal tip housing traversing the camera module, the first light emitting diode being located on one side of the symmetry plane and the second light emitting diode being located on an opposite side of the symmetry plane, a horizontal plane being orthogonal to the symmetry plane and encompassing a center axis of the distal tip housing, the distal tip housing including a tubular wall portion and a distal wall portion distal of the tubular wall portion, the tubular wall portion having an inner wall surface, an outer wall surface, and a wall thickness, and the distal wall portion comprising a window longitudinally aligned with the camera module, wherein the tubular wall portion comprises a first bulged portion, a second bulged portion, and a main portion coextensive at least in part with the first bulged portion and the second bulged portion, the wall thickness at the first bulged portion and the second bulged portion being greater than the wall thickness at the main portion, the first bulged portion and the second bulged portion extending distally from a proximal end of the distal tip housing toward but no further than the window, and wherein a distance between a point on the outer wall surface of the main portion and a central axis of the tubular wall portion defines a first radius of a first circle and a distance between a radially outermost point on the outer wall surface of the at least one bulged portion and the central axis defines a second radius of a second circle, wherein the second radius is greater than the first radius, and wherein the second bulged portion extends distally at least as far as the image sensor.

19. The endoscope of claim 18, wherein the wall thickness at the first bulged portion of the tubular wall portion is at least 25% greater than the wall thickness at the main portion.

20. The endoscope of claim 18, wherein the distal tip housing comprises a portion of a working channel, wherein the distal tip housing comprises a camera module side and a working channel side diametrically opposite the camera module side, the portion of the working channel positioned in the working channel side, the second bulged portion being formed on the camera module side, wherein the endoscope bends in two directions and a diameter of the distal tip housing is less than 3.0 mm.

21. The endoscope of claim 18, wherein the distal tip housing comprises a portion of a working channel, wherein the distal tip housing comprises a camera module side and a working channel side diametrically opposite the camera module side, the portion of the working channel positioned in the working channel side, the second bulged portion being formed on the camera module side, wherein the endoscope bends in four directions and a diameter of the distal tip housing is between 4.0 and 4.5 mm.

* * * * *